United States Patent
Chiarello et al.

(10) Patent No.: US 8,602,640 B2
(45) Date of Patent: Dec. 10, 2013

(54) SENSING SYSTEM AND METHOD

(75) Inventors: Ronald P. Chiarello, Lafayette, CA (US); Christopher Andrew Wacinski, Walnut Creek, CA (US); Charles Eric Boyd, San Francisco, CA (US); Stewart Robin Shearer, Pleasanton, CA (US)

(73) Assignee: Entegris—Jetalon Solutions, Inc., Billerica, MA (US)

( * ) Notice: Subject to any disclaimer, the term of this patent is extended or adjusted under 35 U.S.C. 154(b) by 847 days.

(21) Appl. No.: 12/469,662

(22) Filed: May 20, 2009

(65) Prior Publication Data

US 2010/0296079 A1 Nov. 25, 2010

(51) Int. Cl.
*G01N 25/66* (2006.01)
*G01N 21/75* (2006.01)

(52) U.S. Cl.
USPC ............. 374/17; 374/28; 374/20; 374/120; 374/130; 374/45; 73/335.01; 356/72

(58) Field of Classification Search
USPC ......... 374/16–28, 130, 131, 100, 109, 10, 11, 374/12, 120, 121, 159, 161, 147, 148, 144, 374/45, 61, 141; 73/73, 23.25, 25.01, 73/25.04, 335.01; 356/43, 72
See application file for complete search history.

(56) References Cited

U.S. PATENT DOCUMENTS

| | | | |
|---|---|---|---|
| 3,751,672 A | 8/1973 | Michel et al. | |
| 4,704,029 A | 11/1987 | Van Heuvelen | |
| 4,778,270 A | 10/1988 | Kinney et al. | |
| 4,946,288 A * | 8/1990 | Siska et al. | ........ 374/20 |
| 5,364,510 A | 11/1994 | Carpio | |
| 5,442,435 A | 8/1995 | Cooper et al. | |
| 5,565,978 A | 10/1996 | Okubo et al. | |
| 5,617,201 A | 4/1997 | Kahre | |
| 5,898,503 A | 4/1999 | Keller et al. | |
| 5,912,456 A | 6/1999 | Melendez et al. | |
| 5,922,285 A | 7/1999 | Melendez et al. | |
| 5,946,083 A | 8/1999 | Melendez et al. | |
| 6,024,923 A | 2/2000 | Melendez et al. | |
| 6,045,756 A | 4/2000 | Carr et al. | |
| 6,073,480 A | 6/2000 | Gokhfeld | |
| 6,097,479 A | 8/2000 | Melendez et al. | |
| 6,111,248 A | 8/2000 | Melendez et al. | |

(Continued)

FOREIGN PATENT DOCUMENTS

JP 401170838 A 7/1989
WO WO 2010/135266 A1 11/2010

OTHER PUBLICATIONS

"OptiSonde™ General Eastern Chilled Mirror Hygrometer," *General Electric*, GE Sensing, product brochure, 8 pages, (2007).

(Continued)

*Primary Examiner* — Gail Verbitsky
(74) *Attorney, Agent, or Firm* — Alston & Bird LLP

(57) ABSTRACT

A sensing system is configured to detect physical parameters of a fluid sample. In particular, the sensing system is configured to detect the dew point of the fluid by reducing temperature of a sensing medium and detecting the fluid condensate on a sensing surface by directing light from a light source to the sensing surface and detecting the light reflected off the sensing surface onto a light detector. The light source and the light detector are on the opposite side of the sensing medium from the sensing surface.

24 Claims, 12 Drawing Sheets

(56) References Cited

U.S. PATENT DOCUMENTS

| | | |
|---|---|---|
| 6,111,652 A | 8/2000 | Melendez et al. |
| 6,118,520 A | 9/2000 | Harner |
| 6,183,696 B1 | 2/2001 | Elkind et al. |
| 6,191,847 B1 | 2/2001 | Melendez et al. |
| 6,239,255 B1 | 5/2001 | Furlong et al. |
| 6,267,641 B1 | 7/2001 | Vanell et al. |
| 6,326,612 B1 | 12/2001 | Elkind et al. |
| 6,374,845 B1 | 4/2002 | Melendez et al. |
| 6,386,894 B2 | 5/2002 | Carr |
| 6,401,974 B1 | 6/2002 | Elkind |
| 6,415,235 B1 | 7/2002 | Bartholomew et al. |
| 6,424,416 B1 | 7/2002 | Gross et al. |
| 6,549,276 B1 | 4/2003 | Longtin |
| 6,574,575 B2 | 6/2003 | Deng et al. |
| 6,594,018 B1 | 7/2003 | Bartholomew |
| 6,760,104 B2 | 7/2004 | Gomelskiy |
| 6,885,455 B2 | 4/2005 | Bartholomew et al. |
| 7,064,816 B2 | 6/2006 | Langenbacher et al. |
| 7,144,153 B2 | 12/2006 | Sato |
| 7,184,639 B2 | 2/2007 | Hamada |
| 7,268,864 B2 | 9/2007 | Chiarello et al. |
| 7,317,533 B2 | 1/2008 | Chiarello et al. |
| 7,319,523 B2 | 1/2008 | Chiarello et al. |
| 7,397,547 B2 | 7/2008 | Chiarello et al. |
| 7,471,379 B2 | 12/2008 | Chiarello et al. |
| 7,504,957 B2 | 3/2009 | Veerasamy |
| 2003/0117623 A1 | 6/2003 | Tokhtuev et al. |
| 2004/0042526 A1* | 3/2004 | Zlochin ............. 374/16 |
| 2004/0240515 A1* | 12/2004 | Egan et al. ......... 374/120 |
| 2005/0046853 A1 | 3/2005 | Sato |
| 2005/0053116 A1* | 3/2005 | Tsang et al. ........ 374/20 |
| 2005/0110989 A1 | 5/2005 | Schermer et al. |
| 2005/0179901 A1 | 8/2005 | Ostlin et al. |
| 2006/0094941 A1 | 5/2006 | Cho |
| 2006/0158653 A1 | 7/2006 | Chiarello et al. |
| 2006/0198149 A1 | 9/2006 | Jonsson et al. |
| 2007/0211781 A1* | 9/2007 | Kanai et al. ........ 374/20 |
| 2010/0272608 A1* | 10/2010 | Penterman et al. ... 422/69 |
| 2011/0038392 A1* | 2/2011 | Ando et al. ......... 374/16 |
| 2011/0188535 A1* | 8/2011 | Boehm ............... 374/20 |
| 2012/0210776 A1* | 8/2012 | So et al. ............ 73/73 |

OTHER PUBLICATIONS

Chinowsky, et al., "Performance of the Spreeta 2000 Integrated Surface Plasmon Resonance Affinity Sensor," *Sensors and Actuators B 6954*, pp. 1-9, (2003).

Geake et al., "A Linear Differentiating Refractometer,"*Meas. Sci. Technolo.*, 5 pp. 531-539, Printed in the UK, (1994).

Geake et al., "The Huygens SSP Refractometer," *Proceedings Symposium of Titan*, (1992).

Lorenz, "Raindrops of Titan," *Adv. Space Res.*, 15(3):(3)317-(3)320, (1995).

Meeten et al., "Refractive Index Measurement of Absorbing and Turbid Fluids by Reflection near the Critical Angle," *Meas. Sci. Technol.*, 6:214-221, Printed in the UK, (1995).

PCT International Preliminary Report on Patentability for application PCT/US2010/035168 mailed Dec. 11, 2011.

PCT International Search Report and Written Opinion for application PCT/US2010/035168 mailed Jul. 12, 2010.

\* cited by examiner

SENSING SYSTEM AND METHOD

FIELD OF THE INVENTION

The present invention pertains to the field of sensors, more particularly to optical analytical instrumentation configured to measure physical characteristics, such as saturation point, of a gas mixture.

BACKGROUND OF THE INVENTION

The temperature of a condensation surface, at which the rate of the condensate exactly equals the evaporation, is frequently defined as the dew point temperature or saturation point. Optical condensation type dew point hygrometers, commonly called "chilled mirror" hygrometer, are configured to detect a dew point or saturation point of a gas and are well known in the art of analytical instrumentation. These "chilled mirror" hygrometers are usually configured so the condensation surface is maintained in vapor pressure equilibrium with the analyzed gas.

Referring to FIG. 1, one of the characteristics of the known "chilled mirror" hygrometers is that a light source 4 and a photodetector 8 of these "chilled mirror" hygrometers are on the same side of the mirror 2 as the sample 6. The surface of the mirror 2 in direct contact with the analyzed gas is called a condensation surface 1. In other words, the light from the light source 4 of the "chilled mirror" hygrometer travels through the analyzed gas 6, reflects off the condensation surface 1 of the mirror 2, and travels through the analyzed gas 6 to the photodetector 8. The mirror 2 is usually a metal plate of a highly reflective metal such as gold, rhodium or platinum. In the known "chilled mirror" hygrometers the analyzed gas 6 is in direct contact with the condensation surface 1 of the mirror 2, the light source 4 and the photodetector 8.

In the known "chilled mirror" hygrometers the mirror 2 is usually cooled by a thermoelectric or Peltier cooler 10 until dew or frost starts to condense on the condensation surface 1 of the mirror 2. While the Peltier cooler 10 manipulates the temperature of the mirror 2, the "chilled mirror" hygrometer continuously monitors the condensation surface 1 of the mirror 2 to detect condensation. The temperature of the condensation surface 1 is usually measured with a thermocouple or thermistor 12 embedded in the mirror 2. When the condensate starts to form on the condensation surface 1, the condensate on the condensation surface 1 scatters the light from the light source 4 and reduces the amount of light, detected by the photodetector 8. At the point in time when the photodetector 8 detects the change in the intensity of the light reaching its surface, the "chilled mirror" hygrometer records the temperature of the mirror 2. This recorded temperature is a dew point of the analyzed gas 6.

One of the problems of the known "chilled mirror" hygrometers is that when the analyzed gas 6 is corrosive, the mirror 2 and the other elements of the known "chilled mirror" hygrometer quickly deteriorate from contact with the analyzed gas 6. The other problem is that in many applications where dew point measurements are required the presence of a metal from the metal plate mirror 2 in the test environment is highly undesirable.

The light source 4 and the photodetector 8 are usually insulated from the analyzed sample by epoxy sealants or other protective vapor barriers, such as Mylar® film. However, if the analyzed gas is highly corrosive, these elements of the hygrometer quickly deteriorate. Also the metal plate mirror 2 is in direct contact with the analyzed gas 6, which leaks metal into the tested environment and is unacceptable in many applications.

SUMMARY OF THE INVENTION

The present invention addresses the problems of known sensing systems. The sensing system of this invention can be configured to detect physical parameters of a gaseous sample. The sensing system is useful in semiconductor manufacturing, biopharmaceutical manufacturing, biochemical defense systems, healthcare, petro and oil industry, oil and gas exploration, chemical industry, mining industry, food industry and the like.

The sensing system preferably comprises a sensing medium, a light source, a light detector, a thermal module, a temperature sensor, and a processing unit. A sensing medium preferably has two surfaces, a sensing surface which is in direct contact with a sample and a back surface which is substantially isolated from the sample. The light source and the light detector are positioned to be on the same side of the sensing medium as the back surface, i.e. positioned so that the light emitted by the light source travels through the sensing medium before reaching the sensing surface. According to one preferred embodiment, a thermal module is used to gradually cool the sensing medium. When the temperature of the sensing surface reaches the dew point temperature of the sample, the gaseous sample in direct contact with the sensing surface starts condensing on the sensing surface. The light source emits light that is directed to the sensing surface. The light passing through the sensing medium may be partially or wholly reflected off the condensation surface and directed to the light detector. When condensate forms on the sensing surface, the portion of the light reflected off the sensing surface onto the light detector changes. The sensing system detects the change in the amount or distribution of light striking the light detector and registers the temperature of the sensing medium at the time of this change. Based on the temperature of the sensing surface at the time condensation is first detected, the sensing system may calculate various physical parameters of the sample, including dew point temperature, dry bulb temperature, wet bulb temperature, absolute humidity, relative humidity, water vapor pressure and other physical parameters of the sample.

In some embodiments the sensor system is also capable of measuring a concentration in a liquid condensate forming on the sensing surface, utilizing optical reflectivity to determine Index of Refraction and thereby chemical concentration of the liquid. Some of the methods of measuring a concentration by using optical reflectivity are described in the U.S. Pat. No. 7,319,523 and its child patents, which methods can be utilized with some embodiments of the sensing system of the present invention. The disclosure of U.S. Pat. No. 7,319,523 is hereby incorporated by reference in its entirety.

BRIEF DESCRIPTION OF THE DRAWINGS

Some embodiments of the invention are disclosed in greater detail in the accompanying drawings, in which.

DETAILED DESCRIPTION OF SOME EMBODIMENTS OF THE INVENTION

Figure 1:
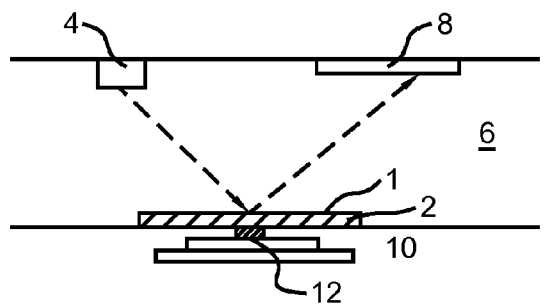
FIG. 1 depicts the prior art humidity sensor.
Figure 2:
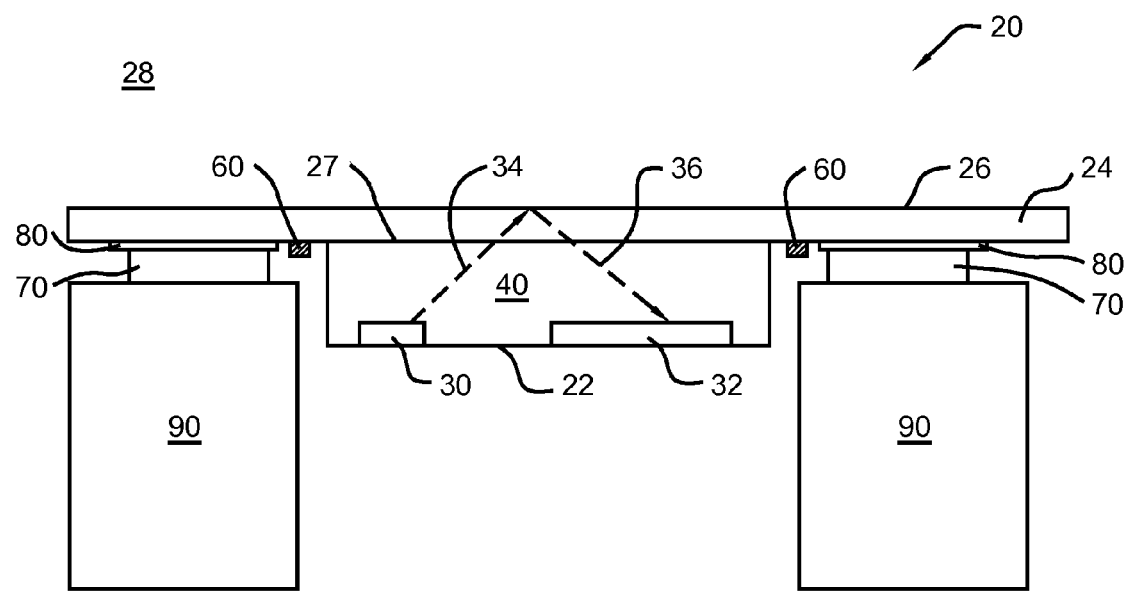
FIG. 2 depicts schematic representation of one of the embodiments of a sensor head.

In preferred embodiment, the sensing system comprises a sensor head 20 shown on FIG. 2. The sensor head 20 comprises a sensing medium 24 having a sensing surface 26 and a back surface 27. The sensing surface 26 is in direct contact with a sample 28, the back surface 27 is substantially isolated from the sample.

Preferably, the sensor head 20 includes at least one light source 30 and at least one light detector 32, capable of detecting the amount of light striking the face of the light detector 32. In a preferred embodiment, the light source 30, the sensing medium 24 and the light detector 32 are arranged so that, in absence of the sample 28, the rays of light 34, emitted by the light source 30, travel to the sensing medium 24, and pass through the sensing medium 24 toward the sensing surface 26. When the rays of light 34 reach the sensing surface 26, they are at least partially reflected off the sensing surface 26 and are directed to the light detector 32.

Figure 2A:
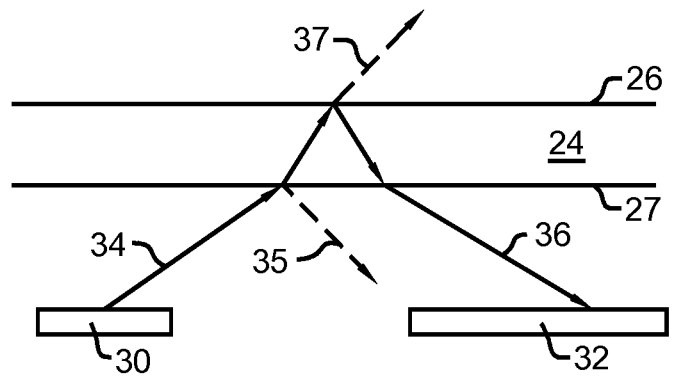
FIGS. 2a-2c depict schematic representation of different states of a sensing surface.

FIG. 2*a* shows how the light travels in the sensor head 20 in absence of the sample 28. The light 34 travels from the light source 30 to the sensing medium 24. At the back surface 27 of the sensing medium 24 the light 34 is partially reflected, forming scattered light 35. The main portion of the light 34 passes through the back surface 27 of the sensing medium 24 and travels towards the sensing surface 26. At the sensing surface the light 34 partially passes through (see rays of light 37) and is partially reflected back into the sensing medium 24. The reflected light 36 travels outside the sensing medium 24 and to the light detector 32.

Figure 2B:
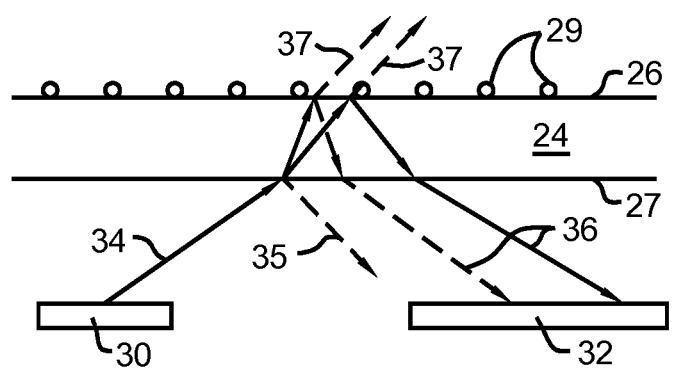

Referring to FIG. 2*b*, when there is condensate 29 present on the sensing surface 26, but the condensate 29 does not cover the sensing surface 26 uniformly, for the rays of light 34 hitting the sensing surface 26 where the condensate 29 is present, at the sensing surface 26 the smaller portion of this light is reflected back to the light detector 32, comparing to the condensate-free state of the sensing surface 26. Also the direction of this reflected light 36 may change. However, the rays of light 34, which hit the sensing surface 26 in the condensate-free spots, reflect back to the light detector 32 as previously. In summary, when condensate 29 is present on the sensing surface 26, the intensity and/or distribution of light hitting the light detector 32 changes in comparison to the condensate-free state of the system.

Figure 2C:
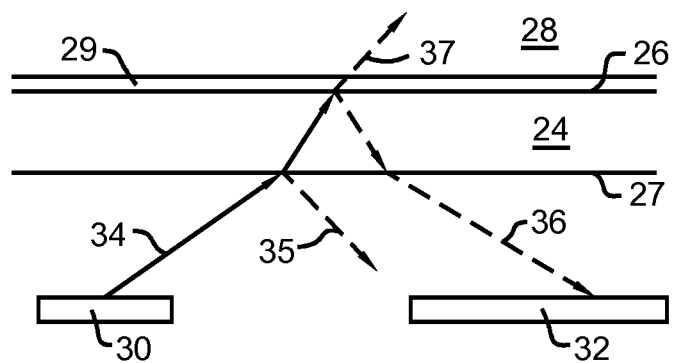

FIG. 2*c* shows the situation where the sensing surface 26 is substantially covered by the condensate 29. Here, a smaller proportion of light 34 is reflected off the sensing surface/condensate interface than when the sensing surface 26 is condensate-free because a portion of light 34 is being refracted by the condensate 29.

Preferably the sensing medium 24 has the form of a plate or a disk. The sensing medium 24 is made of an optically transparent material, which is transparent for at least some of the wavelengths of the light emitted by the light source 30. It is also preferred that the index of refraction of the material of sensing medium 24 is at least as high as the index of refraction of the sample 28.

In one of the embodiments, the material of the sensing medium 24 is also chemically resistant to withstand contact with sample 28. In another embodiment the material of the sensing medium 24 has high mechanical strength and scratch hardness to prolong the lifetime of the sensor head 20 and to minimize possible scratching of the sensing surface 26.

In many applications it is extremely important that the sensing medium 24 does not emit any pollutants into the sample 8. Therefore, in a preferred embodiment the material of the sensing medium 24 is substantially chemically inert.

Known materials used for the sensing medium include, but are not limited to, sapphire, glass, quartz, diamond, silicon, ZnSn, thallium bromoiodide crystals, cadmium telluride, Germanium, AMTIR materials and others. Sapphire is currently preferred for its superior ability to resist chemical attacks, its high durability, scratch resistance and optical integrity. However, this invention is in no way limited to a sapphire sensing medium 24.

The sample 28 can be static or flowing. Preferably, the sample 28 is flowing at a nominal rate. In some embodiments, to ensure the flow of the sample 28, the sensor head 20 is equipped with a sample pump (not shown). The sample pump provides at least a minimum flow of the sample 28 over the sensing surface 26.

Figure 3:
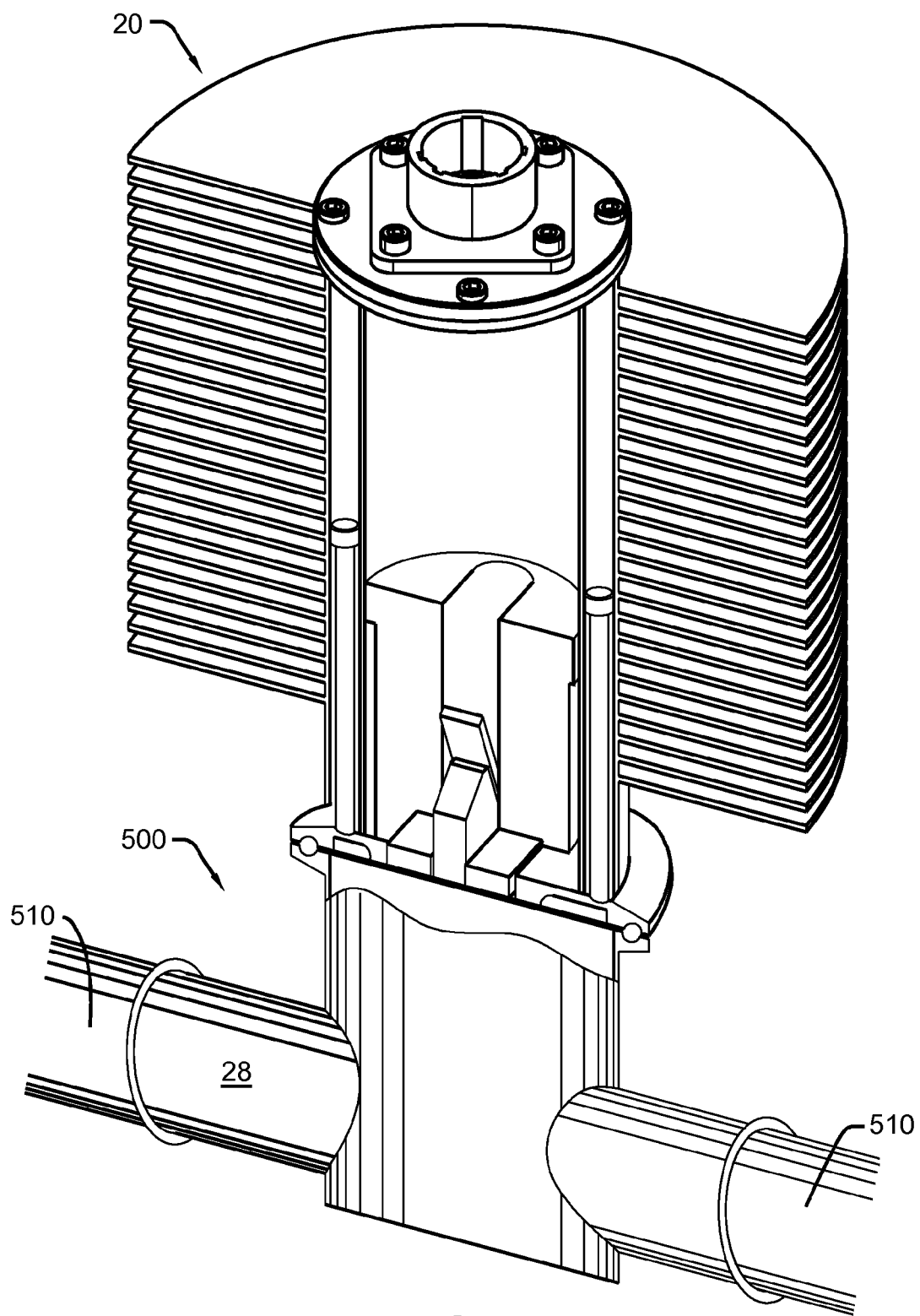
FIG. 3 depicts "tortuous path" embodiment of the sensor head.

In some of the embodiments the sample 28 travels to the condensation surface 26 through a "tortuous path" to emulate the sample's condition in some parts of the chamber where the sample 28 is located. In fast flowing pipes the use of the "tortuous path" can also reduce the speed of the sample's movement and thereby reduce the risk of damage to the sensing medium 24 and increase the accuracy of the measurements. FIG. 3 illustrates the use of the sensor head 20 with a "tortuous path" T-shaped component 500 of a pipe 510 carrying the sample 28.

Preferably, the light source 30 and the light detector 32 are encapsulated within a housing 22 and are isolated from the sample 28 by the sensing medium 24 and/or the housing 22.

FIGS. 4*a*-4*e* show different configurations of the housing 22 and the sensing medium 24. In the embodiment depicted in FIG. 4*a* the housing 22 has an opening, and the sensing medium 24 is coupled to the housing 22 in such manner that the back surface 27 of the sensing medium 24 closes the opening in the housing 22, sealing the inside space 40 of the housing 22 from the sample 28. The inside space 40 of the housing 22 holds the light source 30 and the light detector 32. Preferably, the seal between the back surface 26 and the housing 22 prevents penetration of the sample 28, and also gases, small solid particles, smoke and other pollutants from the sample 28 into the inside space 40 of the housing 22 and from the inside space 40 of the housing 22 into the sample 28 thereby isolating the sample 28 from the sensing system components, located inside the housing 22.

Figure 4A:
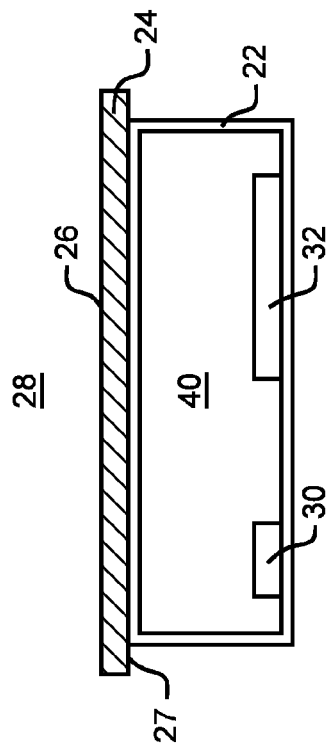
FIGS. 4*a*-4*f* depict schematic representations of other embodiments of the sensor head.
Figure 4B:
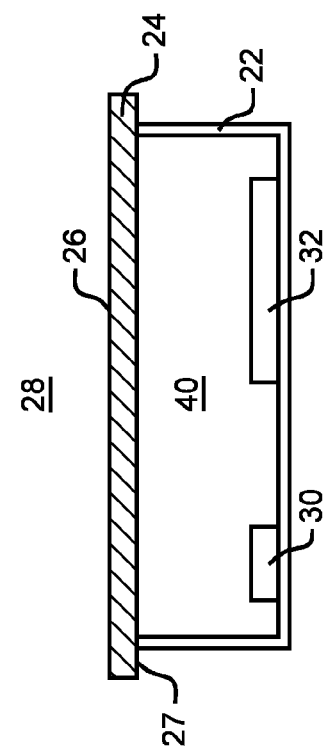

In another embodiment, depicted in FIG. 4*b*, the housing 22 forms an inside space 40, where the inside space 40 is completely enclosed by the housing 22 and holds the light source 30 and the light detector 32. In this embodiment the sensing medium 24 is attached to one of the outside surfaces of the housing 22 in such manner that the back surface 27 of the sensing medium 24 is facing the outside surface of the housing 22 and the sensing surface 26 of the sensing medium 24 is in direct contact with the sample 28.

Figure 4C:
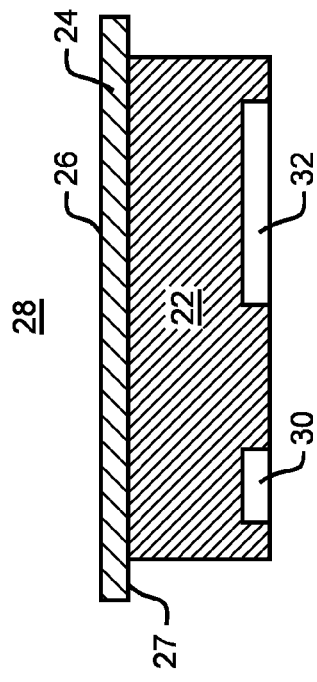

In another embodiment, depicted in FIG. 4*c*, the sensing medium 24 is integrated into one of the walls of the housing 22. Preferably, the sensing surface 26 of the sensing medium 24 is in direct contact with the sample 28 and the back surface 27 of the sensing medium 24 faces the inside space 40 of the housing 22. The inside surface 40 of the housing 22 holds the light source 30 and the light detector 32.

Figure 4D:
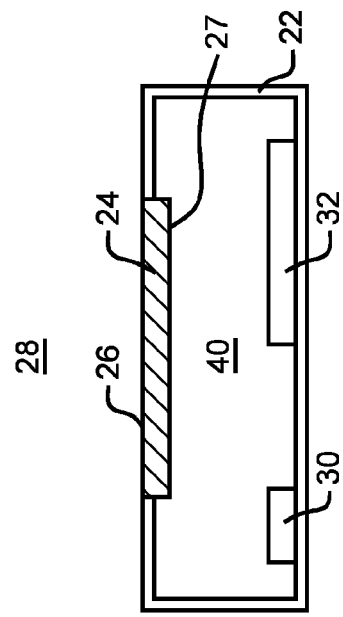

In another embodiment, depicted in FIG. 4d, the housing 22 is an optical housing formed from a monolith of optically clear material, where some of the components of the sensor head 20, such as the light source 30 and the light detector 32 are embedded into the housing 22. In this embodiment the sensing medium 24 is attached to one of the outside surfaces of the optical housing 22 where the back surface 27 of the sensing medium 24 is facing the housing 22 and the sensing surface 26 of the sensing medium 24 is in direct contact with the sample 28.

Figure 4E:
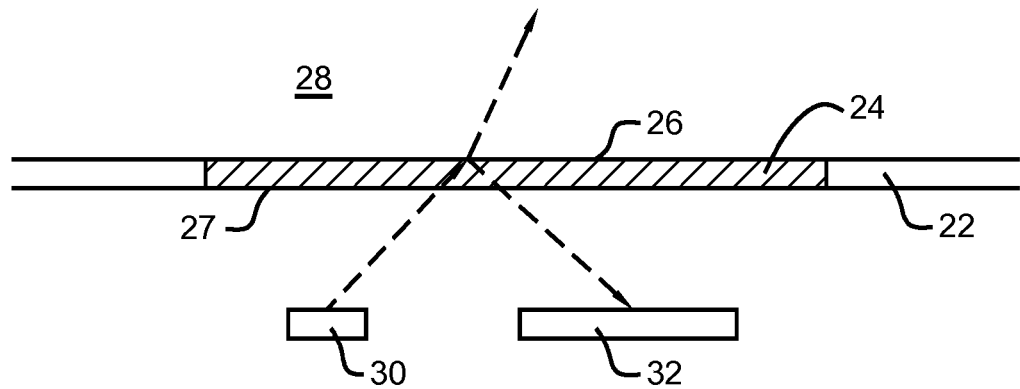

In another embodiment, depicted in FIG. 4e, the sensing medium 24 is integrated into a barrier between the sample 28 and the other components of the sensor head 20. In this embodiment the sensing surface 26 of the sensing medium 24 is in direct contact with the sample while the back surface 27 of the sensing medium 24 faces the light source 30 and the light detector 32.

In another embodiment (not shown) the sensing medium 24 is attached to such barrier 22 on the sample side of the barrier 22. Preferably, the sensing surface 26 of the sensing medium 24 is in direct contact with the sample 28 and the back surface of the sensing medium 24 is facing the barrier 22. The light source 30 and the light detector 32 are on the opposite side of the barrier from the sample 28 and the sensing medium 24.

Figure 4F:
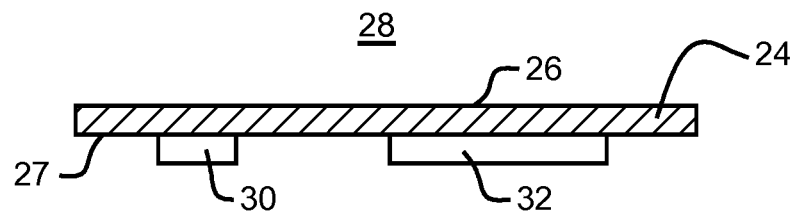

In another embodiment, depicted in FIG. 4f, the light source 30 and the light detector 32 are located in close proximity to the back surface 27 of the sensing medium 24 while the sensing surface 26 of the sensing medium 24 is in direct contact with the sample 28.

In a preferred embodiment, the sensing medium 24 is attached to the housing 22. Preferably, the sensing medium 24 is mechanically attached to the housing 22 by an optically clear adhesive. In other embodiments, the sensing medium 24 is attached to the housing 22 by other methods. In one of the embodiments the sensing medium 24 is formed directly on the housing 22. For instance, in one of the embodiments the sensing medium 24 is deposited directly onto the housing 22 by one of the known deposition methods.

Figure 5A:
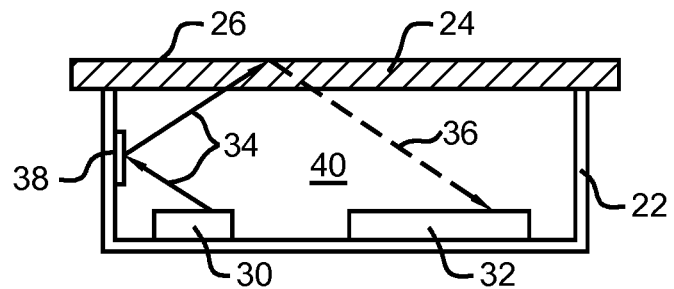
FIGS. 5*a*-5*c* depict schematic representations of other embodiment of the sensor head.
Figure 5B:
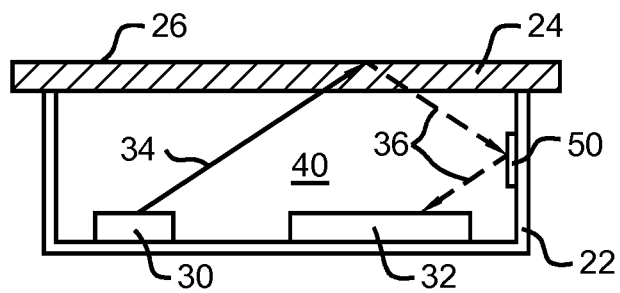
Figure 5C:
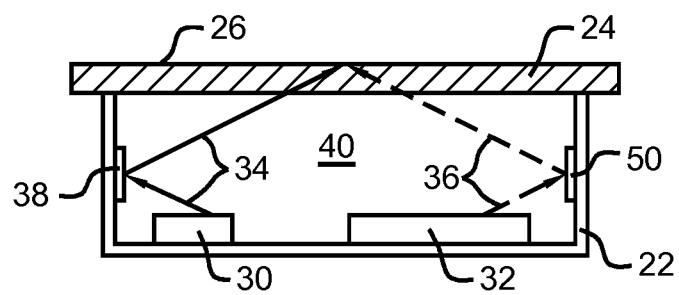

In some of the embodiments the sensor head 20 comprises at least one mirror to direct the light from the light source 30 to the light detector 32. FIGS. 5a-5c depict some examples of the sensor head 20 configurations. In one of the embodiments, the light 34 emitted by the light source 30 is reflected off a first mirror 38 before reaching the sensing medium 24 (see FIG. 5a). In another embodiment the reflected light 36 is directed toward a second mirror 50 and then is redirected towards the light detector 32 (see FIG. 5b). In another embodiment the sensor head 20 includes two mirrors, the first mirror 28 and the second mirror 30 (see FIG. 5c) and the light 34 originating from the light source 30 travels to the first mirror 38 and then to the sensing medium 24, and the reflected light 36 travels first to the second mirror 50 and then to the light detector 32.

However the present invention is not limited to the configurations of mirrors specifically recited in this specification.

Returning to FIG. 2, the light source 30 can be implemented by different types of light sources, such as light sources producing, for instance, visible light, colored light, infra-red light, and other types of light sources producing light in other parts of the light spectrum.

In one of the embodiments the sensor head 20 includes more than one light source 30. Preferably, the different light sources produce light of different spectrums. Alternatively, in some embodiments, the multiple light sources 30 produce the same type of light. In some embodiments multiple light sources 30 are spread within the housing thereby covering a larger index of refraction range. In other embodiments the light sources 30 are placed in close proximity to each other.

In some embodiments the light detector 32 is implemented with a photodetector. In other embodiments the light detector 32 is a charge-coupled device (CCD). The light detector 32 can be implemented, for example, with a single light detecting element, a one-dimensional array of detecting elements or a two-dimensional array.

In another embodiment the light detector 32 is a single cell photodetector. In one other embodiment the light detector 32 is a light detector capable of determining whether the amount of light striking its surface exceeds the predetermined value or not, i.e. in this embodiment the light detector 32 has a binary output. Also, a combination of light detectors of different types and geometries can be used with the system of the present invention.

Photodetectors that can be used with the system of the present invention include, for example, TSL 1401CS-LF, TSL213, TSL401, and TSL1401 (manufactured by Texas Instruments Inc. Dallas, Tex.). CCDs that can be used with the present invention include, for example, CCD 111 and CCD 3041 (manufactured by Fairchild Imaging of Milpitas, Calif.).

Preferably, the light detector 32 is a two-dimensional CCD array. However, this invention is not limited to the specific types and configurations of the light detectors mentioned above.

In a preferred embodiment at least parts of the housing 22 are impenetrable to visible light and/or, in some embodiments, to other types of radiation. Preferably, the housing 22 blocks the passage of all light from the outside into the inside space 40 of the housing 22 except for at least part of the area of the housing 22 in direct contact with the sensing medium 24. This feature of the sensor head 20 reduces interference of the outside radiation with the readings of the light detector 32.

The sensor head 20 also includes at least one temperature sensor 60 arranged in close proximity to the sensing medium 24 and capable of detecting the temperature of the sensing surface 26 of the sensing medium 24. In a preferred embodiment the temperature sensor 60 is in direct contact with the sensing medium 24. Preferably the sensor head 20 includes two or more temperature sensors 60 to more accurately assess the temperature of the sensing surface 26. In some embodiments, at least one of the temperature sensors 26 is capable of measuring temperature of the sample 28. In some embodiments the same temperature sensor 26 is used to measure the temperature of the sensing surface 26 and the temperature of the sample 28, consecutively or simultaneously.

The sensor head 20 also includes at least one thermal module (TM) 70, arranged in close proximity to the sensing medium 24. A thermal module is a device that moves heat from one side of the device to the other side of the device against the temperature gradient. Preferably, the TM 70 is capable of heating and cooling the sensing medium 24 at a predetermined speed to a predetermined temperature. In a preferred embodiment the TM 70 is a thermoelectric or Peltier module or a heat pump. In some embodiments, the sensor 20 comprises two-stage or three-stage TMs to widen the range of applications of the sensing system.

In one of the embodiments, the sensor head 20 includes two or more TMs 70 to achieve faster and more precise heating/cooling of the sensing medium 24. In another embodiment the TM 70 (or multiple TMs) substantially covers the back surface 27 of the sensing medium 24.

The sensor head 20 may also comprise at least one slug 80 arranged between the TM 70 and the back surface 27 of the sensing medium 24. In one of the embodiments the slug 80 is a plate made of material with high thermal conductivity, such as aluminum or copper. The slug 80 assists with more even distribution of the heat from the TM 70 to the sensing medium 24.

In a preferred embodiment the sensor head 20 also comprises at least one thermal management device, such as, for example, a heat sink, a forced air cooling device, a convective air cooling device, or a liquid cooling device. Preferably, the thermal management of the sensor head 20 is performed by at least one heat sink 90. The heat sink 90 absorbs and dissipates heat from the TM 70. FIGS. 6-9 depict different embodiments of heat sinks 90 that can be used with the present sensing system. However, other configurations of heat sinks can be used with this sensing system. Also other thermal management devices can be used with this sensing system. In some embodiments a combination of different thermal management devices, such as a heat sink and a liquid cooling device, can be used.

Figure 6:
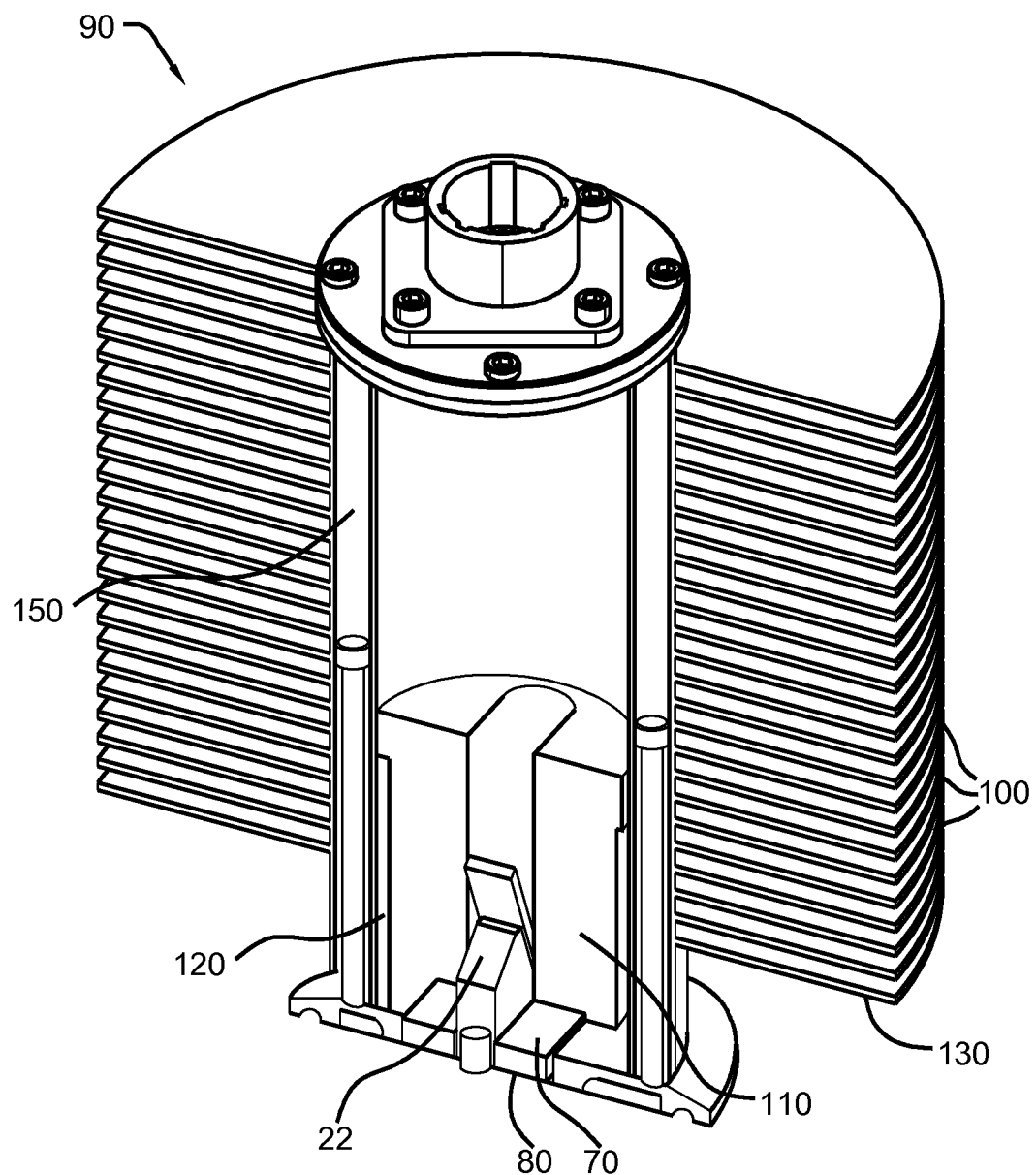
FIGS. 6-7, 9 depict schematic representations of different the embodiments of the sensor head with a stacked fins heat sink.

FIG. 6 shows a cross-section of the sensor head 20 with a stacked fins heat sink 90. The heat sink 90 has a TM side and the back side, where the TM side is arranged in close proximity to the TM 70, and the back side is facing away from the TM 70. In this embodiment the heat sink 90 comprises a plurality of fins 100 that are interlocked together to form a stacked fin array. Preferably, the fins 100 are ring-shaped objects attached to a central part 150. The central part 150 is preferably cylindrical. In a preferred embodiment the fins 100 and the central part 150 are made of materials with high thermal conductivity, such as aluminum or copper. Preferably the central part 150 is located in close proximity to the TMs 70.

In a preferred embodiment the central part 150 of the heat sink 90 also comprises a cylindrical cavity 120, which forms a gap separating the core 110 of the central part 150 from the outside portion of the heat sink 90, including the fins 100 and the outside portion of the central part 150. This cavity 120 starts on the TM side of the heat sink 90 and rises at least above the first fin 130 on the TM side of the fin array. Preferably, the core part of the heat sink 90 is in direct contact with the TM 70.

This cavity 120 improves heat removal from the TMs 70 to the fins 100 by preventing the back flow of the heat to the TMs 70 through the outside portions of the central part 150 of the heat sink 90. In other words, the core 110 of the heat sink 90 connects with the rest of the heat sink structure only above the first fin 130, and this way the heat from the core 110 is directed to the fins 100 and is subsequently dissipated, and this heat does not have a chance to leak back to the TMs 70.

Figure 7:
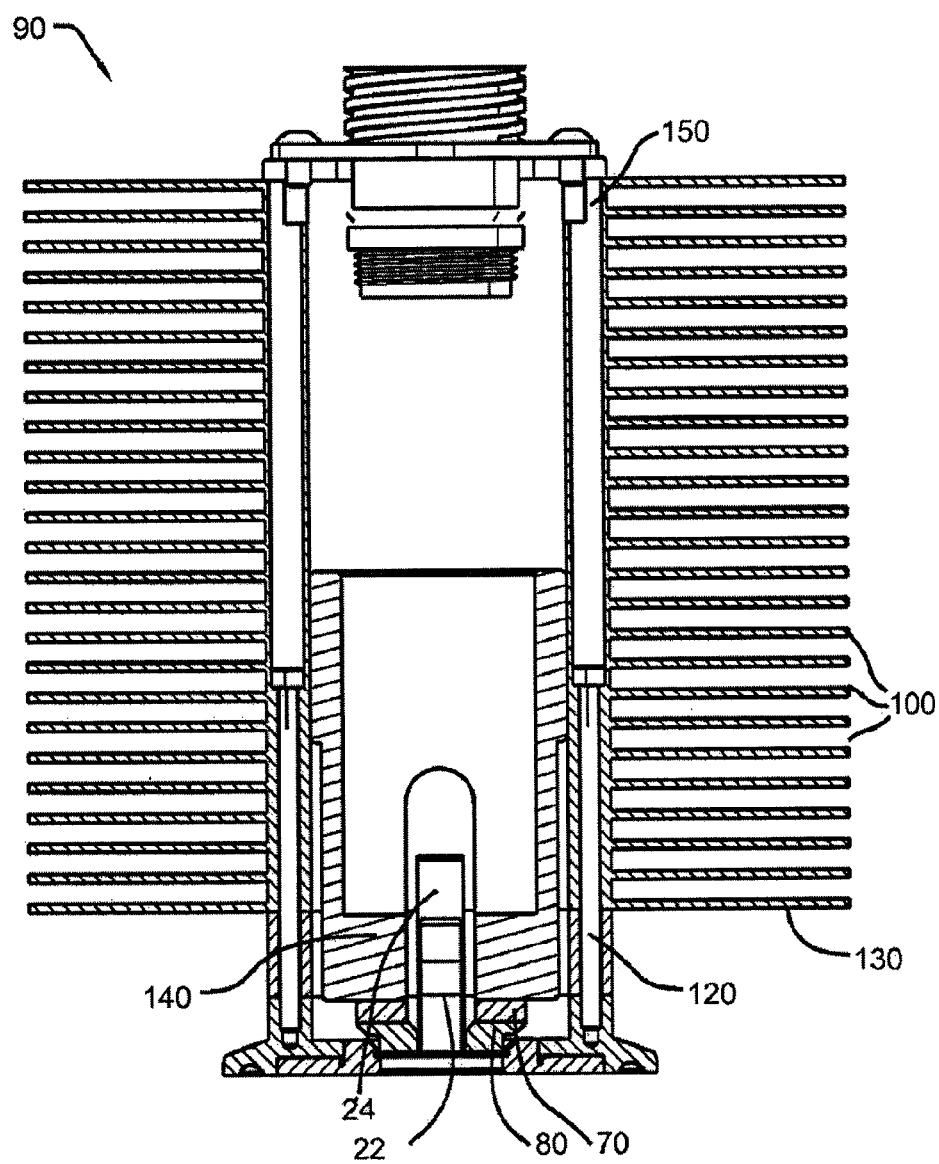

In another embodiment, depicted on FIG. 7, the heat sink 90 is implemented as a two-module device: a fin module 105, comprising a cylindrical central part 150 and fins 100, and a piston 140, which can be inserted in the center of the fin module 105. Preferably, the fin module 105 and the piston 140 are made of a material with high thermal conductivity. The piston 140 can be made from the same material as the fin module 105 or from a different material. Preferably, when the piston 140 is inserted in the center of the fin module 105, the upper portion of the piston 140 is in contact with the fin module 105. At the same time there is a gap between the lower portion of the piston 140 and the fin module 105 forming a cylindrical cavity 120. Preferably, the cavity 120 starts from the TM side of the heat sink 90 and rises above the first fin 130 on the TM side of the fin module 105.

Figure 8A:
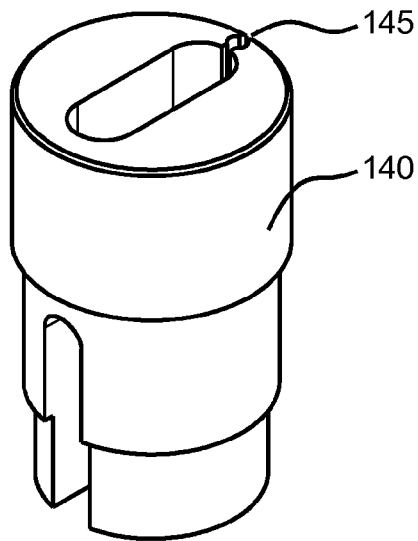
FIGS. 8*a*-8*b* depicts a schematic representation of an expandable piston.
Figure 8B:
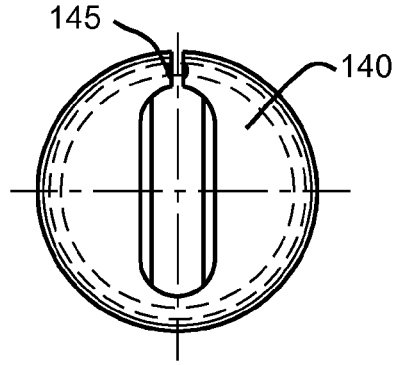

In a preferred embodiment the piston 140 is expandable to ensure sufficient thermal contact of the piston 140 with the fin module 105. FIGS. 8a and 8b depict one of the embodiments of the expandable piston 140. The piston 140 has a vertical slit 145. After the piston 140 in inserted into the cylindrical cavity 120, parting element, such as a wedge or a screw, is inserted into the slit 145 thereby making the piston 140 expand. Expanding piston 140 creates a better metal-on-metal contact with the fin module 105.

In some embodiments, where the piston 140 and the fin module 105 are not in direct contact in at least some parts of the cavity 120, it is preferred to place thermal grease between the upper part of the piston 140 and the fin module to improve their thermal contact. One of the advantages of the two-module heat sink is that it is easier to manufacture than a one-piece heat sink 90, where the cavity 120 has to be machined.

Figure 9:
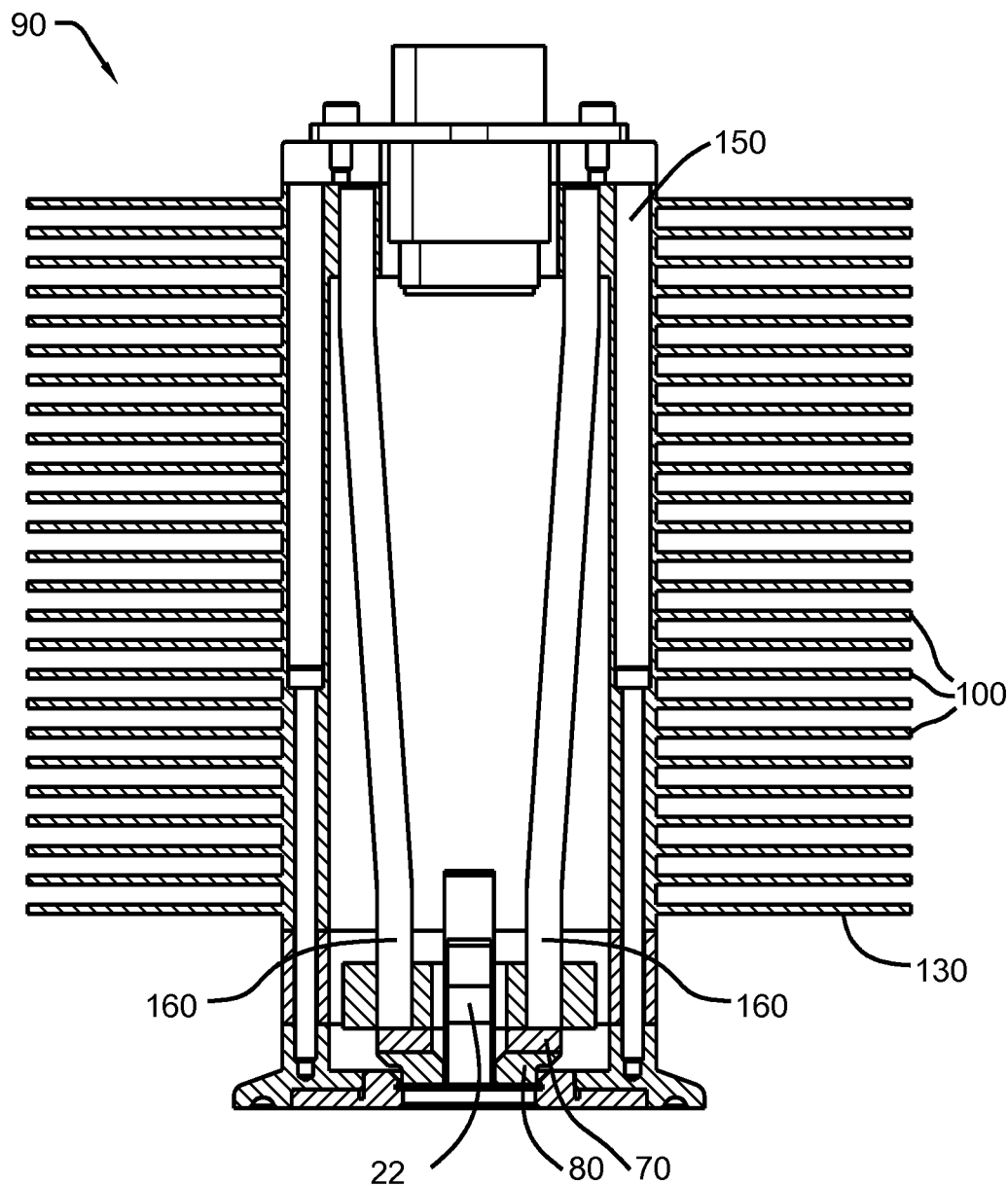

FIG. 9 depicts another embodiment of the heat sink 90. In this embodiment the heat sink 90 has a hollow center and at least one heat pipe 160 running from the TM side of the heat sink 90 to the back side of the heat sink 90. The heat pipes 160 transfer heat from the TM side of the heat sink 90, which is in contact with the TMs 70, to the back side of the heat sink 90. This configuration of the heat sink 90 reduces the leakage of the heat back to the TMs 70.

Returning to FIG. 2, in some embodiments the temperature sensors 60 and the TMs 70 are isolated from the sample 28 by a barrier such as a wall of a pipe carrying the sample 28 or a wall of a chamber containing the sample 28. In other embodiments the temperature sensors 60, the TMs 70 and other elements of the sensor head 20, located outside the housing 22, are not separated from the sample 28 by a pre-existing barrier. In these configurations, it is sometimes preferred for these elements of the system to be additionally isolated from the sample 28. The isolation of these elements from the sample 28 can be implemented by different types of barrier films and epoxy sealants. For instance, boPET films such as Mylar® and Melinex® films can be used.

Figure 10:
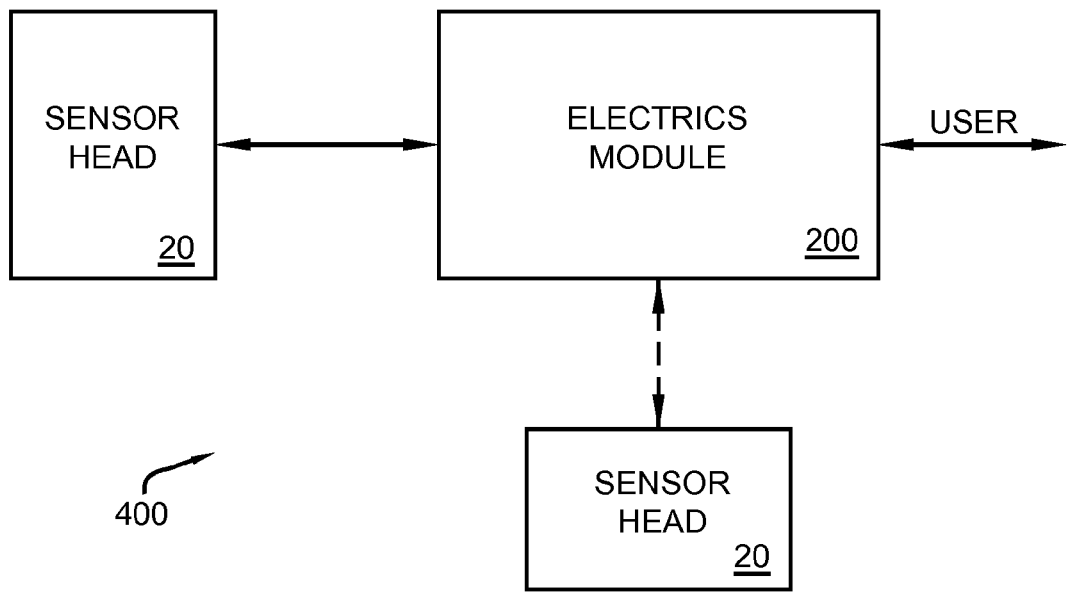
FIG. 10 depicts block diagram of the sensing system.

Preferably the sensing system 400 also comprises a processing unit. In a preferred embodiment the processing unit is implemented as an Electronics Module 200 (see FIG. 10). The Electronics Module 200 can comprise software, hardware and/or firmware components. The sensor head 20 is capable of communicating data to the Electronics Module 200 and of receiving data from the Electronics Module 200. Preferably the communications between the sensor head 20 and the Electronics Module 200 are digital signals. The communications between the sensor head and the Electronics Module 200 are wireless communications and/or communications by wire and/or fiber. In some embodiments the Electronics Module 200 is in the same location as the sensor head 20. In other embodiments the Electronics Module 200 is at a different location from the sensor head 20. In some embodiments an Electronics Module 200 is in communication with more than one sensor head 20.

Preferably the Electronics Module 200 is capable of communicating data to the system user and capable of receiving instructions and data from the user. The user interface can be a separate module or can be incorporated in the Electronics Module 200. The user interface can be physically located directly on the sensor head 20 or it can be in a remote location and communicate with the rest of the system wirelessly or by wires.

Figure 11:
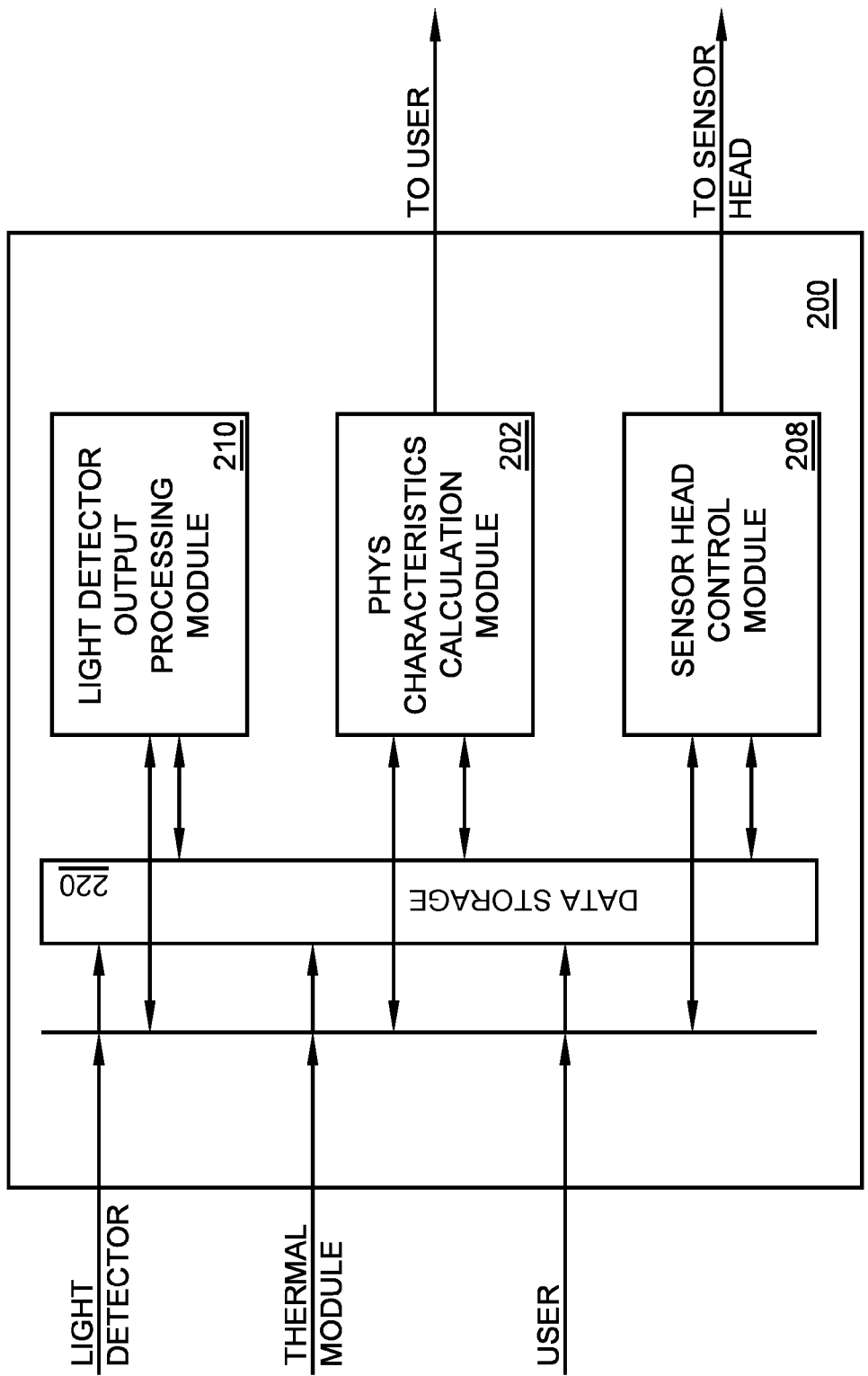
FIG. 11 depicts block diagram of an Electronics Module.

Referring to FIG. 11, preferably, the Electronics Module 200 comprises a Light Detector Output Processing Module 210, a Physical Characteristics Calculation Module 202, and a Sensor Head Control Module 208. In a preferred embodiment the Electronics Module 200 also includes a Data Storage Module 220.

The Light Detector Output Processing Module 210 analyzes output signal of the light detector 32. This module receives the output of the light detector 32 from the sensor head 20, which preferably includes signals produced by at least some of the sensing areas, such as pixels, of the light detector 32. These signals are proportionate to the intensity of the radiation striking the corresponding areas of the light detector 32. In a preferred embodiment the signal, produced by the light detector 32 is a digital signal. In other embodiments the signal is an analogue signal, and it is digitized by the Electronics Module 200. The communications between the light detector 32 and the Electronics Module 200 are implemented wirelessly and/or by wire and/or fiber. Preferably the Light Detector Output Processing Module 210 also receives the corresponding data regarding locations of the sensing areas producing the signals. Alternatively, the Electronics Module 200 can contain previously assembled information about locations of the sensing areas.

Using the information received from the light detector 32, the Light Detector Output Processing Module 210 detects changes in the intensity of the radiation striking the light detector 32.

In one embodiment, the Light Detector Output Processing Module 210 recognizes a change in the light striking the light detector 32 by summing up the signals received from the light detector 32. In this embodiment, first the Light Detector Output Processing Module 210 calculates the total signal S1 from the light detector 32 produced at time t1 by adding the individual signals received by the Electronics Module 200 from the segments of the light detector 32 at time t1. Then it stores S1 and t1 in the Data Storage Module 220. Next, after a predetermined period of time $\Delta t$ elapses, the Light Detector Output Processing Module 210 calculates the total signal S2 at time t2, were t2=t1+$\Delta t$, retrieves S1 from the Data Storage Module 220 and compares S1 and S2. When S1 exceeds S2 by the predetermined value $\Delta S$ or more, the Light Detector Output Processing Module 210 registers a change in the light intensity. If the difference between S1 and S2 is less than $\Delta S$, then after period of time $\Delta t$ elapses, the Light Detector Output Processing Module 210 captures the next set of signals from the light detector 32, calculates its corresponding total signal and compares it to the initial total signal S1.

In some embodiments the Light Detector Output Processing Module 210 also stores the differences between the total signals and/or absolute values of the total signals at corresponding times in the Data Storage Module 220.

In some embodiments the Light Detector Output Processing Module 210 calculates the total signal from the light detector 32 based on less than all signals received from the segments of the light detector 32. In some embodiments the Light Detector Output Processing Module 210 pre-selects a set of representative pixels and only uses output from these pixels to calculate the total signal. In a preferred embodiment these pre-selected pixels are a group of pixels on one of the sides of the light detector 32.

It has been found that in some embodiments that some areas of the light detector 32 are less affected by the change in radiation signal than other areas. When these areas of the light detector 32 are eliminated from the calculation of the total signal S, this elimination can improve the resolution of the sensing system 400 of the present invention.

In some embodiments the area of the light detector 32, selected to be used to calculate S is chosen based on characteristics of the sample 28 being analyzed by the system 400. Preferably, the user of the sensing system 400 can select the area of the light detector 32 to be used to produce the total signal S.

In other embodiments, the Light Detector Output Processing Module 210 also analyzes the distribution of radiation striking the light detector 12. In this case, the Light Detector Output Processing Module 210 calculates total signals for each individual pixel, or a group of pixels located next to each other, and registers a change in signal for each pixel or group of pixels.

The Physical Characteristics Calculation Module 202 receives temperature data from the temperature sensor 60 and records it in the Data Storage Module 220. When the Light Detector Output Processing Module 210 registers a change in light intensity at time t, it communicates this event to the Physical Characteristics Calculation Module 202 which in turn marks the temperature of the sensing medium 24 at the time t as registered by the temperature sensor 24 as a raw dew point temperature of the sample 28 at time t. When the sensor head 20 comprises more than one temperature sensor 24, the Physical Characteristics Calculation Module 202 can use a mean of the temperatures read by these sensors, one of the temperature readings, or other configurations. In other embodiments, at least one of the temperature sensors 24 measures temperature of the sample 28. The Physical Characteristics Calculation Module 202 uses the temperature of the sensing surface 26 and, in some embodiments, the temperature of the sample 28, registered by one or more of temperature sensors 24, to calculate at least some of the following physical characteristics of the sample 28, such as dew point temperature, dry bulb temperature, wet bulb temperature, absolute humidity, relative humidity, water vapor pressure and/or others. Preferably the Electronics Module 200 is capable of transmitting these calculated physical characteristics to the other parts of the system 400 and/or to the user.

In some embodiments the Physical Characteristics Calculation Module 202 is configured to use the data from the temperature sensors 24, including temperature of the sensing surface 26 and/or temperature of the sample 28, and the data from the Light Detector Output Processing Module 210 to calculate concentration in the liquid sample 28, accumulating on the sensing surface 26. Some of the methods of measuring concentration are described in the U.S. Pat. No. 7,319,523 and its child patents, which methods can be utilized with some embodiments of the sensing system of the present invention. In a preferred embodiment, the Sensor Head Module 208 is capable of generating signals to the Sensor Head 20 and/or its components, such as light source 30, light detectors 32, temperature sensors 60, and/or TMs 70. These signals are transmitted to the Sensor Head 20 and/or its components wirelessly and/or by wire or fiber. In a preferred embodiment, the Sensor Head Module 208 is configured to generate such signals at least partially based on the use input. In some embodiments, the Sensor Head Module 208 generates these signal based on predetermined operation scheme. In other embodiments the Sensor Head Module 208 generates these signals based on the Sensor Head Module input from other components of the system 20.

In a preferred embodiment the Sensor Head Module 208 receives as an input the signals from the LD Output Processing Module 210, the Physical Characteristics Calculation Module 202, the Data Storage 220, and/or the system users. In some embodiments the Sensor Head Module 208 receives input from the Sensor Head 20 or its components.

For example, in some embodiments the Sensor Head Module 208 is configured to generate signals to the light source 30, where the light source 30 changes the intensity of the produced light based on the signal received from the Sensor Head Module 208. In some embodiments, the Sensor Head Module 208 generates such signal to the light source 30 in response to a signal from a user. In other embodiments the Sensor Head Module 208 generates some signals based on the signal from the Light Detector Output Processing Module 210.

In a preferred embodiment, when the Light Detector Output Processing Module 210 detects a change in the light detector output signal, it also sends a signal to the Sensor Head Control Module 208. The Sensor Head Control Module 208 is configured to generate control signals to the Sensor Head 20.

In one of the embodiments, the Sensor Head Control Module 208 receives from the user an expected dew point temperature and receives the current temperature data from the temperature sensor 24. Using this data, the Sensor Head Control Module 208 preferably generates a Reset control signal to TM 70 to set the temperature of the TM 70 above the expected dew point temperature by the predefined value T. As a result the temperature of the sensing medium 24 also rises above the expected dew point by T. Then the Sensor Head Control Module 208 generates control signals to the TM 70 to gradually decrease TMs temperature at predetermined speed V ("down-slope signals"). Accordingly, the temperature of the sensing medium 24 gradually decreases. When the Sensor Head Control Module 208 receives a signal from the Light Detector Output Processing Module 210 that a change in the output of the light detector 32 has been detected, the Sensor Head Control Module 208 again generates the Reset control signal to raise the temperature of the TM and of the sensing medium 24 and then receives the down-slope signals to repeat the cycle.

Figure 12:
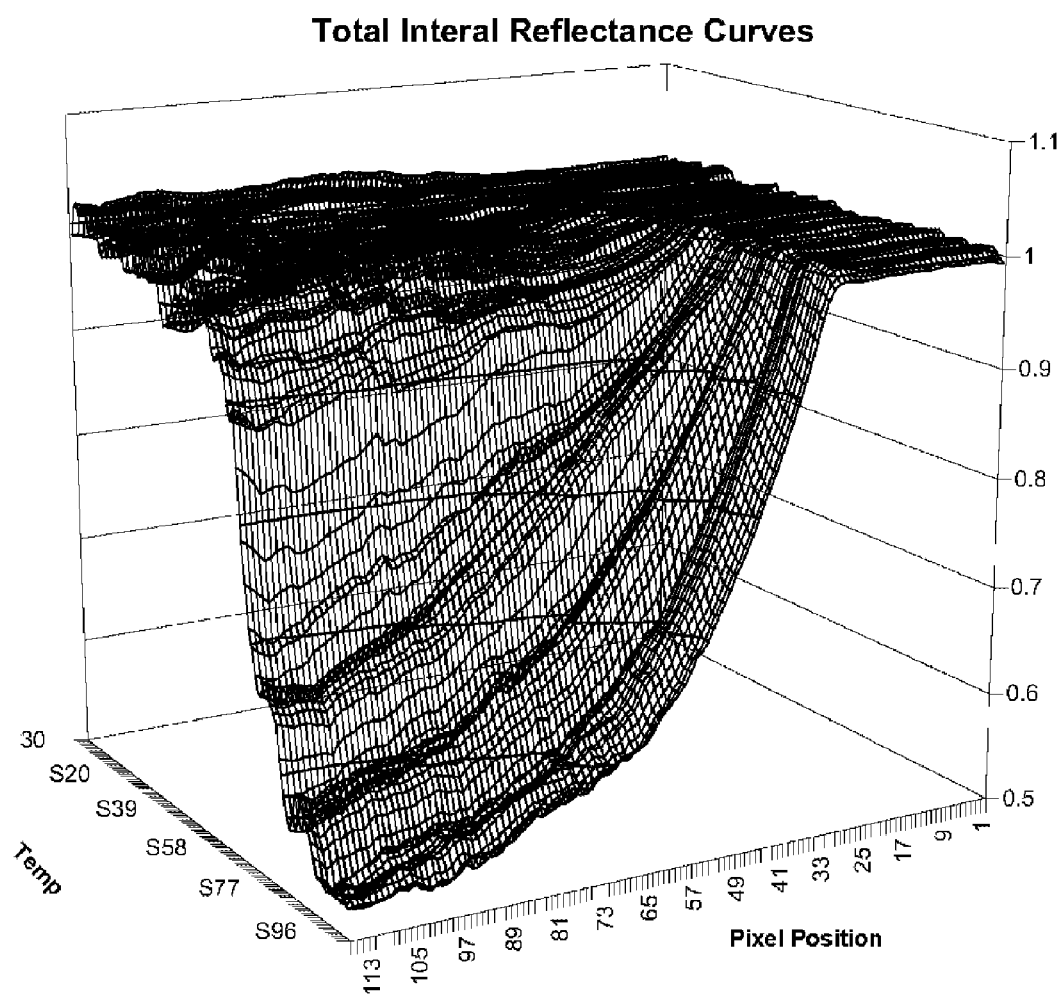
FIG. 12 depicts reflectance curves of the sensing system.

In some embodiments the Sensor Head Control Module 208 generates the Reset control signal and then the "down-slope signals" at predetermined times. In other embodiments the Sensor Head Control Module 208 repeats this cycle periodically at predetermined intervals. In some embodiments the system is so configured that the user can initiate the Reset-down slope cycle. FIG. 12 depicts total internal reflectance curves. In these curves the light intensity of the individual pixels is plotted as a function of pixel position and temperature of the sensing medium 24. As can be seen in these curves, pixels on the left (pixel positions 113 and less) are more reactive to the temperature change. In a preferred embodiment, the sensor system 400 is configured to analyze reactivity of the different segments of the light detector 32 and determine which part of the light detector array is more responsive to the appearance of condensate and, accordingly, which part of signals produced by the light detector 32 should be used by the Light Detector Output Processing Module 210 to generate the total signal S.

The invention claimed is:

1. A system comprising:
a sensing medium comprising at least two surfaces, a sensing surface capable of being in direct contact with a sample and a back surface substantially isolated from the sample;
at least one sensor arranged to collect temperature information for use in determining a temperature of the sensing surface;
at least one thermal module arranged to alter the temperature of the sensing surface;
at least one light source configured to emit light through the sensing medium to the sensing surface such that at least a portion of the light reflects from the sensing surface onto at least one light detector when the sensing surface is not in direct contact with the sample;
the at least one light detector having a light detector output, the light detector output comprising a light detector signal indicative of a measure of light detected by the light detector;
a processing unit having as an input the light detector signal and the temperature information and having a processing unit output, the processing unit output comprising output information from which at least one physical characteristic of the sample can be determined;
wherein the light source and the light detector are separated from the sample by the sensing medium; and
a heat sink arranged to at least partially remove heat from the at least one thermal module, wherein the heat sink includes a central part, wherein the sensing medium, the at least one sensor, the at least one thermal module and the at least one light source are located within the central part.

2. The system of claim 1, wherein the output information is configured to determine dew point of the sample.

3. The system of claim 1, wherein the output information is configured to determine concentration of the sample.

4. The system of claim 1, wherein the output information is configured to determine dew point of the sample and concentration of the sample.

5. The system of claim 1 wherein the sensing medium is made of dielectric material.

6. The system of claim 1 wherein the sensing medium is made of sapphire.

7. The system of claim 1 wherein the sensing medium is made of quartz.

8. The system of claim 1 wherein the sensing medium is made of glass.

9. The system of claim 1 further comprising at least one slug arranged between the sensing medium and the at least one thermal module.

10. The system of claim 1 wherein the processing unit comprises a light detector output processing module.

11. The system of claim 1 wherein the processing unit comprises a physical characteristics calculation module.

12. The system of claim 1 wherein the processing unit comprises a thermal module control module.

13. The system of claim 1 further comprising:
a sensor head comprising the sensing medium, the at least one sensor, the at least one thermal module, the at least one light source and the at least one light detector, and
wherein the processing unit is in communication with more than one sensor head.

14. The system of claim 1, wherein the central part of the heat sink is cylindrical.

15. The system of claim 1, wherein the heat sink comprises an outside portion connected to the central part of the heat sink and the outside portion comprises a plurality of fins.

16. The system of claim 15, wherein the plurality of fins are interlocked together to form a stacked fin array.

17. The system of claim 1, wherein the central part of the heat sink comprises:
a core; and
a cavity that forms a gap separating the core from an outside portion of the heat sink.

18. The system of claim 1, wherein the central part of the heat sink comprises a piston that is configured to expand to provide contact with an outside portion of the heat sink.

19. The system of claim 1, wherein the heat sink comprises:
a hollow center; and
at least one heat pipe extending from a first side of the heat sink to the back side of the heat sink, wherein the heat pipe is configured to transfer heat from the first side of the heat sink to the back side of the heat sink.

20. The system of claim 1, wherein the output information is based on the light detector signal and the temperature information.

21. A sensing method comprising:
increasing temperature of a sensing surface of a sensing medium above a predetermined level, wherein the sensing surface of the sensing medium is in direct contact with a sample;
gradually decreasing the temperature of the sensing surface using a thermal module;
detecting light emitted by a light source through the sensing medium to the sensing surface of the sensing medium;
generating a detected light signal based on the detected light;
detecting temperature of the sensing surface using a sensor;
generating a detected temperature signal based on the detected temperature;
outputting sample information from which at least one physical characteristic of the sample can be determined;
wherein the sample information is at least partially based on the detected light signal and the detected temperature signal; and
wherein the light source is separated from the sample by the sensing medium; and
removing heat from the thermal module using a heat sink having a central part, wherein the sensing medium, the sensor, the thermal module and the light source are located within the central part.

22. The method of claim 21 further comprising using the sample information to determine dew point of the sample.

23. The method of claim 21 further comprising using the sample information to determine a concentration of the sample.

24. The method of claim 21 further comprising using the sample information to determine dew and concentration of the sample.

* * * * *

UNITED STATES PATENT AND TRADEMARK OFFICE
CERTIFICATE OF CORRECTION

| | | |
|---|---|---|
| PATENT NO. | : 8,602,640 B2 | Page 1 of 1 |
| APPLICATION NO. | : 12/469662 | |
| DATED | : December 10, 2013 | |
| INVENTOR(S) | : Chiarello et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 820 days.

Signed and Sealed this
Fourteenth Day of April, 2015

Michelle K. Lee
*Director of the United States Patent and Trademark Office*